United States Patent
Koehn et al.

(10) Patent No.: US 10,556,874 B2
(45) Date of Patent: Feb. 11, 2020

(54) N-(1,3,4-OXADIAZOL-2-YL)ARYL CARBOXAMIDE DERIVATIVES WITH HERBICIDAL ACTION

(71) Applicant: Bayer CropScience Aktiengesellschaft, Monheim am Rhein (DE)

(72) Inventors: Arnim Koehn, Klein-Winternheim (DE); Christian Waldraff, Bad Vilbel (DE); Hartmut Ahrens, Egelsbach (DE); Ines Heinemann, Hofheim (DE); Ralf Braun, Ramberg (DE); Hansjoerg Dietrich, Liederbach am Taunus (DE); Christopher Hugh Rosinger, Hofheim (DE); Elmar Gatzweiler, Bad Nauheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 173 days.

(21) Appl. No.: 15/738,618

(22) PCT Filed: Jun. 29, 2016

(86) PCT No.: PCT/EP2016/065091
§ 371 (c)(1),
(2) Date: Dec. 21, 2017

(87) PCT Pub. No.: WO2017/005564
PCT Pub. Date: Jan. 12, 2017

(65) Prior Publication Data
US 2018/0179171 A1    Jun. 28, 2018

(30) Foreign Application Priority Data
Jul. 3, 2015 (EP) .................................... 15175277

(51) Int. Cl.
| | | |
|---|---|---|
| *C07D 271/113* | (2006.01) |
| *A01N 43/82* | (2006.01) |
| *C07D 413/12* | (2006.01) |
| *C07D 417/12* | (2006.01) |
| *A01N 47/12* | (2006.01) |
| *A01N 47/06* | (2006.01) |
| *A01N 41/06* | (2006.01) |
| *A01N 43/42* | (2006.01) |
| *A01N 43/56* | (2006.01) |
| *A01N 43/80* | (2006.01) |
| *A01N 47/28* | (2006.01) |

(52) U.S. Cl.
CPC .......... *C07D 271/113* (2013.01); *A01N 41/06* (2013.01); *A01N 43/42* (2013.01); *A01N 43/56* (2013.01); *A01N 43/80* (2013.01); *A01N 43/82* (2013.01); *A01N 47/06* (2013.01); *A01N 47/12* (2013.01); *A01N 47/28* (2013.01); *C07D 413/12* (2013.01); *C07D 417/12* (2013.01)

(58) Field of Classification Search
CPC .. C07D 271/113; C07D 413/12; A01N 47/06; A01N 47/12; A01N 43/82; A01N 41/06; A01N 43/42; A01N 43/56; A01N 43/80; A01N 25/32
See application file for complete search history.

(56) References Cited

U.S. PATENT DOCUMENTS

| | | | | |
|---|---|---|---|---|
| 5,739,394 A | * | 4/1998 | Lui ....................... | C07C 43/313 562/586 |
| 7,378,530 B2 | * | 5/2008 | Macherla .............. | C07C 257/06 548/182 |
| 9,101,141 B2 | | 8/2015 | Koehn et al. | |
| 9,204,650 B2 | | 12/2015 | Koehn et al. | |
| 9,896,466 B2 | * | 2/2018 | Neuzil ................. | C07F 9/5442 |
| 2014/0080705 A1 | | 3/2014 | Koehn et al. | |
| 2014/0371068 A1 | | 12/2014 | Koehn et al. | |

FOREIGN PATENT DOCUMENTS

| | | |
|---|---|---|
| WO | 2012126932 A1 | 9/2012 |
| WO | 2013087577 A1 | 6/2013 |
| WO | 2014126070 A1 | 8/2014 |

OTHER PUBLICATIONS

PCT International Search Report for PCT/EP2016/065091, dated Aug. 11, 2016.
Fryer, et al., "Weed Control Handbook," 5th Edition, Blackwell Scientific Publications, (1968), vol. 1: 101-103.

* cited by examiner

*Primary Examiner* — Mina Haghighatian
*Assistant Examiner* — Nathan W Schlientz
(74) *Attorney, Agent, or Firm* — McBee Moore & Vanik IP, LLC

(57) ABSTRACT

N-(1,3,4-Oxadiazol-2-yl)arylcarboxamide derivatives of the general formula (I) are described as herbicides.

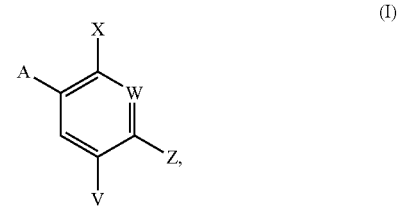

(I)

In this formula (I), V, X and Z represent radicals such as hydrogen, organic radicals such as alkyl, and other radicals such as halogen. A represents an oxadiazole radical. W is CY or N.

13 Claims, No Drawings

N-(1,3,4-OXADIAZOL-2-YL)ARYL CARBOXAMIDE DERIVATIVES WITH HERBICIDAL ACTION

CROSS-REFERENCE TO RELATED APPLICATIONS

This application is a National Stage entry of International Application No. PCT/EP2016/065091, filed Jun. 29, 2016, which claims priority to European Patent Application No. 15175277.1, filed Jul. 3, 2015.

BACKGROUND

Field

The invention relates to the technical field of the herbicides, especially that of the herbicides for selective control of weeds and weed grasses in crops of useful plants.

Description of Related Art

N-(1,3,4-Oxadiazol-2-yl)arylcarboxamides are known as herbicides from WO 2012/126932 A1. WO 2013/087577 A1 discloses also as herbicides N-(1,3,4-oxadiazol-2-yl)arylcarboxamides substituted on the amide nitrogen. Herbicidally active triazinone carboxamides substituted on the amide nitrogen are known from WO 2014/126070 A1.

SUMMARY

It was an object of the present invention to provide herbicidally active compounds having properties improved over those of the compounds disclosed in the prior art.

It has now been found that certain N-(1,3,4-oxadiazol-2-yl)arylcarboxamide derivatives, which have been substituted by specific radicals on the oxadiazoly radical or on the carbamoyl group, are particularly well suited as herbicides.

Accordingly, the present invention relates to N-(1,3,4-oxadiazol-2-yl)arylcarboxamide derivatives of the formula (I)

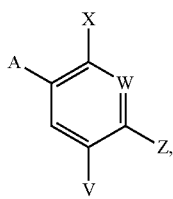

(I)

where the symbols and indices are each defined as follows:
W is N or CY,
X and Z are each independently hydrogen, nitro, halogen, cyano, formyl, thiocyanato, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1R^2$, $P(O)(OR^5)_2$, or heteroaryl, heterocyclyl or phenyl, each substituted by s radicals from the group of methyl, ethyl, methoxy, nitro, trifluoromethyl and halogen,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $CO_2R^1$, $OCO_2R^1$, $NR^1CO_2R^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, CH=$NOR^1$, $(C_1-C_6)$-alkyl-CH=$NOR^1$, $(C_1-C_6)$-alkyl-O—N=$C(R^1)_2$, $(C_1-C_6)$-alkyl-phenyl, $(C_1-C_6)$-alkylheteroaryl, $(C_1-C_6)$-alkylheterocyclyl, phenyl, heteroaryl or heterocyclyl, where the latter 6 radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, or Y and Z together with the two atoms to which they are bonded form a 5-, 6- or 7-membered, unsaturated, partly saturated or saturated ring which, as well as carbon atoms, in each case has s nitrogen atoms, n oxygen atoms, n sulfur atoms and n $S(O)$, $S(O)_2$, C=N—$R^8$, $C(OR^9)_2$, C[—O—$(CH_2)_2$—O—] or C(O) elements as ring members,
wherein the carbon atoms are in each case substituted by s radicals from the group consisting of halogen, cyano, $(C_1-C_6)$-alkyl, $(C_2-C_{10})$-alkenyl, $(C_2-C_{10})$-alkynyl, $(C_1-C_6)$-haloalkyl, $(C_1-C_6)$-alkoxy, phenoxy, halo-$(C_1-C_6)$-alkoxy, $(C_3-C_8)$-cycloalkyl, $(C_2-C_8)$-alkoxyalkyl and phenyl,
wherein the nitrogen atoms are in each case substituted by n radicals from the group consisting of $(C_1-C_6)$-alkyl and phenyl, and in which the aforementioned phenyl radicals are in each case substituted by s radicals from the group consisting of cyano, nitro, halogen, $(C_1-C_6)$-alkyl, $(C_1-C_6)$-haloalkyl and $(C_1-C_6)$-alkoxy,
V is hydrogen, nitro, halogen, cyano, $(C_1-C_4)$-alkyl, $(C_1-C_4)$-haloalkyl or $OR^1$, $S(O)_nR^2$,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups,
$R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-$ $C_6$)-alkyl-$NR^3$-heterocyclyl, where the 21 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl bears n oxo groups, $R^3$ is hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, $R^4$ is ($C_1$-$C_6$)-alkyl, ($C_2$-$C_6$)-alkenyl or ($C_2$-$C_6$)-alkynyl, ($C_3$-$C_6$)-cycloalkyl or ($C_3$-$C_6$)-cycloalkyl-($C_1$-$C_6$)-alkyl, $R^5$ is ($C_1$-$C_4$)-alkyl, n is 0, 1 or 2, s is 0, 1, 2 or 3, A is an A1, A2, or A3 radical

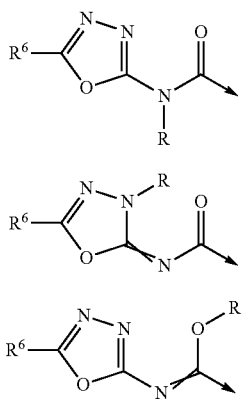

R is ($C_1$-$C_6$)-alkyl-$OC(O)N(R^3)_2$ or ($C_1$-$C_6$)-alkyl-$OC(O)OR^{10}$, $R^6$ is hydrogen, ($C_1$-$C_6$)-alkyl, $R^1O$—($C_1$-$C_6$)-alkyl, $CH_2R^7$, ($C_3$-$C_7$)-cycloalkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, $OR^1$, $NHR^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, $R^7$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, ($C_1$-$C_6$)-alkoxy, ($C_3$-$C_6$)-cycloalkyl, or heteroaryl, heterocyclyl or phenyl, each substituted by s radicals from the group consisting of methyl, ethyl, methoxy, trifluoromethyl and halogen, $R^8$ is ($C_1$-$C_6$)-alkyl, halo-($C_1$-$C_6$)-alkyl, ($C_1$-$C_6$)-alkoxy or halo-($C_1$-$C_6$)-alkoxy, $R^9$ is ($C_1$-$C_6$)-alkyl or halo-($C_1$-$C_6$)-alkyl, $R^{10}$ is ($C_1$-$C_6$)-alkyl, halo-($C_1$-$C_6$)-alkyl or ($C_1$-$C_6$)-cycloalkyl.

DETAILED DESCRIPTION OF A PREFERRED EMBODIMENT

Preference is given to compounds of the general formula (I) in which
$R^6$ is hydrogen, ($C_1$-$C_6$)-alkyl, $R^1O$—($C_1$-$C_6$)-alkyl, halo-($C_1$-$C_6$)-alkyl or ($C_2$-$C_6$)-alkenyl,
and the other substituents and indices have the respective definitions given above.

Particular preference is given to compounds of the general formula (I) in which
W is CY,
X and Z are each independently hydrogen, halogen, ($C_1$-$C_6$)-alkyl, ($C_1$-$C_6$)-haloalkyl, ($C_2$-$C_6$)-alkenyl, ($C_3$-$C_6$)-cycloalkyl, ($C_3$-$C_6$)-halocycloalkyl, $OR^1$, $S(O)_nR^2$, $SO_2N(R^1)_2$, $NR^1SO_2R^2$, $NR^1COR^1$, ($C_1$-$C_6$)-alkyl-$S(O)_nR^2$, ($C_1$-$C_6$)-alkyl-$OR^1$, or heteroaryl, heterocyclyl or phenyl, each substituted by s radicals from the group of methyl, ethyl, methoxy, nitro, trifluoromethyl and halogen,
Y is hydrogen, ($C_2$-$C_6$)-alkenyl, $COR^1$, $CO_2R^1$, $OCO_2R^1$, $NR^1CO_2R^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $S(O)_nR^2$, $SO_2N(R^1)_2$, ($C_1$-$C_6$)-alkyl-$S(O)_nR^2$, ($C_1$-$C_6$)-alkyl-$OR^1$, ($C_1$-$C_6$)-alkyl-$OCOR^1$, ($C_1$-$C_6$)-alkyl-$CO_2R^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, $N(R^1)_2$, $CH$=$NOR^1$, ($C_1$-$C_6$)-alkyl-$CH$=$NOR^1$, ($C_1$-$C_6$)-alkylheteroaryl, ($C_1$-$C_6$)-alkylheterocyclyl, heteroaryl or heterocyclyl, where the 4 latter radicals are each substituted by s radicals from the group consisting of halogen, nitro, cyano, ($C_1$-$C_6$)-alkyl, ($C_1$-$C_6$)-cycloalkyl, $S(O)_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl bears n oxo groups,
V is hydrogen, Cl, OMe, methyl or ethyl,
$R^6$ is methyl, ethyl, methoxymethyl or methoxyethyl,
and the other substituents and indices have the respective definitions given above.

Very particularly preference is given to compounds of the general formula (I) in which
X is F, Cl, Br, methyl, ethyl, cyclopropyl, trifluoromethyl, methoxy, methoxymethyl, methoxyethoxymethyl, SMe or $SO_2Me$,
Z is hydrogen, F, Cl, Br, I, methyl, ethyl, trifluoromethyl, difluoromethyl, pentafluoroethyl, methylsulfonyl or ethylsulfonyl,
Y is hydrogen, SMe, S(O)Me, $SO_2Me$, SEt, S(O)Et, $SO_2Et$, $CH_2OMe$, $CH_2OEt$, $CH_2OCH_2CF_3$, $CH_2SMe$, $CH_2S(O)Me$, $CH_2SO_2Me$, vinyl, C(O)Me, C(O)Et, C(O)cPr, $CO_2Me$, CHN=OMe, 4,5-dihydro-1,2-oxazol-3-yl, 5-methyl-4,5-dihydro-1,2-oxazol-3-yl, 5-methyl-4,5-dihydro-1,2-oxazol-3-yl, 5-cyanomethyl-4,5-dihydro-1,2-oxazol-3-yl, 4,5-dihydro-1,2-oxazol-5-yl, 3-methyl-4,5-dihydro-1,2-oxazol-5-yl, 1H-pyrazol-1-yl, 1H-1,2,3-triazol-1-yl, 2H-1,2,3-triazol-2-yl, 1H-1,2,4-triazol-1-yl, pyrolidin-2-on-1-yl, morpholin-3-on-4-yl, OMe, OEt, OnPr, $OCH_2cPr$, $OCH_2CH_2F$, $OCH_2CH_2OMe$ or $OCH_2CH_2CH_2OMe$,
V is hydrogen,
R is $CH_2OCO_2Et$, $CH(CH_3)OCO_2Me$, $CH(CH_3)OCO_2Et$, $CH(CH_3)OCO_2$-c-hexyl, $CH(CH_3)OCO_2$-i-Pr or $CH(CH_3)OCO_2$-t-Bu,
$R^6$ is methyl,
and the other substituents and indices have the respective definitions given above.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen represents fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned. The same applies to the formation of ring systems by different atoms and elements.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically. Owing to the oxime ether structure, the compounds of the invention may also occur as geometric isomers (E/Z isomers). The invention also relates to all E/Z isomers and mixtures thereof which are encompassed by the general formula (I) but not defined specifically.

The compounds according to the invention may be prepared, for example, by the method shown in scheme 1, by reacting an N-(1,3,4-oxadiazol-2-yl)arylcarboxamide (IV) with a compound of the general formula (III), where L is a leaving group, for example a chlorine, bromine, iodine, mesyloxy, tosyloxy, trifluorosulfonyloxy, etc.:

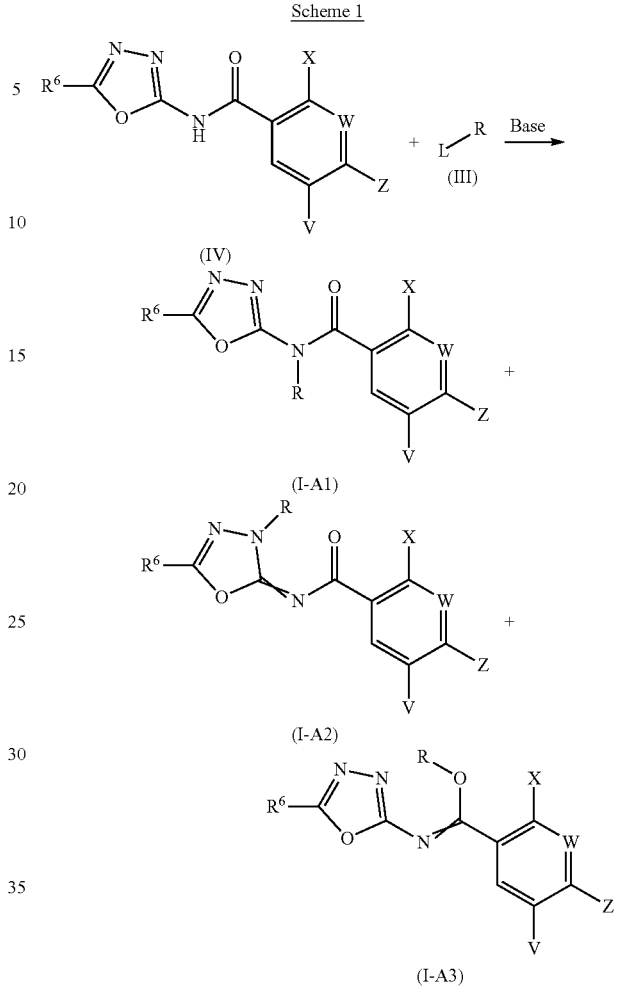

The compounds of the formula (I) according to the invention are obtained in principle as a mixture of the compounds of formulae (I-A1), (IA-2) and (I-A3) and may be isolated by simple methods known to those skilled in the art such as chromatographic separation or recrystallization.

The N-(1,3,4-oxadiazol-3-yl)arylcarboxamides of the formula (IV) are known in principle and may be prepared by the methods described in WO 2012/126932 A1. The compounds of the formula (III) in which L is a leaving group such as chlorine, bromine, iodine, methylsulfonyloxy, tosyloxy or trifluorosulfonyloxy are either commercially available or can be prepared by known methods described in the literature.

Collections of compounds of the formula (I) which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from Perkin Elmer, Waltham, Mass. 02451, USA. For the parallelized purification of compounds of the general formula (I) or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the general formula (I) can take place completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described herein gives compounds of the formula (I) in the form of substance collections, which are called libraries. The present invention also provides libraries comprising at least two compounds of the formula (I).

The compounds according to the invention of the formula (I), referred to hereinbelow as "compounds according to the invention", have an excellent herbicidal effectiveness against a broad spectrum of economically important mono- and dicotyledonous annual weeds. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active compounds can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds of the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. It is preferred to employ the compounds of the invention as herbicides in crops of useful plants which are resistant, or have been made resistant by genetic engineering, to the phytotoxic effects of the herbicides.

It is preferred to use the compounds of the invention in economically important transgenic crops of useful plants and ornamentals, for example of cereals such as wheat, barley, rye, oats, millet/sorghum, rice, cassava and corn or else crops of sugar beet, cotton, soybean, oilseed rape, potato, tomato, peas and other vegetables. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659), transgenic crop plants, for example cotton, capable of producing *Bacillus thuringiensis* toxins (Bt toxins), which make the plants resistant to particular pests (EP-A-0142924, EP-A-0193259).

transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature, for example, the abovementioned novel properties ("gene stacking") through combinations.

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition Cold Spring Harbor Laboratory Press, Cold Spring Harbor, N.Y., or Winnacker "Gene and Klone [Genes and clones]", VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227, Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active compounds of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

A further advantage of the compounds according to the invention also consists of a lower toxicity towards organisms such as insects, amphibians, fish and mammals.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th Ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophillite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E.

Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active compound concentration is, for example, about 10% to 90% by weight, the remainder to 100% by weight consisting of customary formulation constituents. In emulsifiable concentrates, the active compound concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active compound content depends partially on whether the active compound is in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. Chemical Examples

1. Synthesis of ethyl 1-{[2-methyl-3-(methylsulfonyl)-4-(trifluoromethyl)benzoyl](5-methyl-1,3,4-oxadiazol-2-yl)amino}ethyl carbonate (Table Example No. 1-145), ethyl 1-[5-methyl-2-{[2-methyl-3-(methylsulfonyl)-4-(trifluoromethyl)benzoyl]imino}-1,3,4-oxadiazol-3(2H)-yl]ethyl carbonate (Table Example No. 4-145) and 1-[(ethoxycarbonyl)oxy]ethyl-2-methyl-N-(5-methyl-1,3,4-oxadiazol-2-yl)-3-(methylsulfonyl)-4-(trifluoromethyl)benzenecarboximidate (Table Example No. 7-145)

To a solution of 1.00 g (2.752 mmol) of 2-methyl-N-(5-methyl-1,3,4-oxadiazol-2-yl)-3-(methylsulfonyl)-4-(trifluoromethyl)benzamide are in 20 ml of acetonitrile are added at room temperature 882 mg (5.78 mmol) of 1-chloroethyl ethyl carbonate and 799 mg (5.78 mmol) of potassium carbonate and the mixture is boiled under reflux for 9 h. The reaction mixture is concentrated and then dissolved in 20 ml of ethyl acetate and 20 ml of water are added and extracted. The aqueous phase is extracted twice more with 20 ml of ethyl acetate each time. The combined organic phases are washed with saturated NaCl solution, dried and concentrated. The residue is purified by RP-HPLC (acetonitrile/water).

Compound No. 1-145

Yield: 170 mg (12%)

$^1$H-NMR (400 MHz; CDCl$_3$): 7.73 ppm (d, 1H), 7.53 ppm (d, 1H), 7.05-6.92 (broad, 1H), 4.32-4.26 (m, 2H); 3.21 (s, 3H); 2.80 (s, 3H), 2.43 (s, 3H), 1.62 (d, 3H), 1.36 (t, 3H).

Compound No. 4-145

Yield: 180 mg (12.3%)

$^1$H-NMR (400 MHz; CDCl$_3$): 8.04 ppm (d, 1H), 7.81 ppm (d, 1H), 6.74 (q, 1H), 4.25-4.18 (m, 2H); 3.25 (s, 3H); 2.92 (s, 3H); 2.49 (s, 3H); 1.77 (d, 3H), 1.30 (t; 3H).

Compound No. 7-145

Yield: 110 mg (7.9%)

$^1$H-NMR (400 MHz; CDCl$_3$): 7.80 ppm (d, 1H); 7.54 ppm (d, 1H), 7.16 (q, 1H), 4.27 (q, 2H); 3.24 (s, 3H); 2.73 (s, 3H); 2.40 (s, 3H); 1.73 (d, 3H), 1.34 (t; 3H).

2. Synthesis of 1-{[2-chloro-3-(methylsulfinyl)-4-(trifluoromethyl)benzoyl](5-methyl-1,3,4-oxadiazol-2-yl)amino}ethyl ethyl carbonate (Table Example No. 1-385), ethyl 1-[5-methyl-2-{[2-chloro-3-(methylsulfinyl)-4-(trifluoromethyl)benzoyl]imino}-1,3,4-oxadiazol-3(2H)-yl]ethyl carbonate (Table Example No. 4-385) and 1-[(ethoxycarbonyl)oxy]ethyl-2-chloro-N-(5-methyl-1,3,4-oxadiazol-2-yl)-3-(methylsulfinyl)-4-(trifluoromethyl)benzenecarboximidate (Table Example No. 7-385)

By analogy to the abovementioned preparation method, by reacting 1.00 g (2.719 mmol) of 2-chloro-N-(5-methyl-1,3,4-oxadiazol-2-yl)-3-(methylsulfinyl)-4-(trifluoromethyl)benzamide with 871 mg (5.71 mmol) of 1-chloroethyl ethyl carbonate, isolated were:

Compound No. 1-385

Yield: 210 mg (13%)

1H-NMR (400 MHz; CDCl3): 7.70 ppm (d, 1H); 7.63 ppm (d, 1H), 7.12-6.91 (broad, 1H), 4.28 (q, 2H); 3.07 and 3.05 (2s, 3H); 2.46 (s, 3H); 1.66 and 1.64 (2d, 3H); 1.34 (t; 3H).

Compound No. 4-385

Yield: 200 mg (13.7%)

1H-NMR (400 MHz; CDCl3): 7.96 ppm (d, 1H); 7.74 ppm (d, 1H), 6.74 (q, 1H), 4.26-4.18 (m, 2H); 3.13 (s, 3H); 2.49 (s, 3H); 1.77 (d, 3H), 1.30 (t; 3H).

Compound No. 7-385

Yield: 130 mg (9.4%)

1H-NMR (400 MHz; CDCl3): 7.78-7.75 ppm (2d, 1H); 7.66-7.62 ppm (2d, 1H), 7.18 (2q, 1H), 4.31-4.24 (2q, 2H); 3.08 (s, 3H); 2.42 (s, 3H); 1.74 (2d, 3H), 1.34 (2t; 3H).

3. Synthesis of 1-{[2-chloro-3-(methylsulfinyl)-4-(trifluoromethyl)benzoyl](5-methyl-1,3,4-oxadiazol-2-yl)amino}ethyl cyclohexyl carbonate (Table Example No. 3-385), 1-[2-{[2-chloro-3-(methyl-sulfinyl)-4-(trifluoromethyl)benzoyl]imino}-5-methyl-1,3,4-oxadiazol-3(2H)-yl]ethyl cyclohexyl carbonate (Table Example No. 6-385) and 1-{[(cyclohexyloxy)carbonyl]oxy}ethyl-2-chloro-N-(5-methyl-1,3,4-oxadiazol-2-yl)-3-(methylsulfinyl)-4-(trifluoromethyl)benzenecarboximidate (Table Example No. 9-385)

By analogy to the abovementioned preparation method, by reacting 1.00 g (2.719 mmol) of 2-chloro-N-(5-methyl-1,3,4-oxadiazol-2-yl)-3-(methylsulfinyl)-4-(trifluoromethyl)benzamide with 1180 mg (5.71 mmol) of 1-chloroethyl cyclohexyl carbonate, isolated were:

Compound No. 3-385
Yield: 190 mg (10%)
$^1$H-NMR (400 MHz; CDCl$_3$): 7.74 ppm (d, 1H); 7.65 ppm (d, 1H), 7.21-6.89 (broad, 1H), 4.71-4.66 (m, 1H); 3.05 and 3.07 (2s, 3H); 2.48 (s, 3H), 2.00-1.88 (m, 2H), 1.80-1.71 (m, 2H), 1.70-1.20 (m, 9H).

Compound No. 6-385
Yield: 50 mg (3.3%)
$^1$H-NMR (400 MHz; CDCl$_3$): 7.96 ppm (d, 1H); 7.74 ppm (d, 1H), 6.74 (q, 1H), 4.64-4.59 (m, 1H); 3.13 (s, 3H); 1.93-1.20 (m, 13H).

Compound No. 9-385
Yield: 180 mg (12%)
$^1$H-NMR (400 MHz; CDCl$_3$): 7.78-7.75 ppm (2d, 1H); 7.65-7.62 ppm (2d, 1H), 7.18 (2q, 1H), 4.70-4.66 (m, 1H); 3.08 (s, 3H); 2.42 (s, 3H); 1.94-1.92 (m, 2H), 1.78-1.73 (m, 5H), 1.59-1.26 (m, 6H).

The examples listed in the tables below were prepared analogously to the abovementioned methods or are obtainable analogously to the abovementioned methods. The compounds listed in the tables below are very particularly preferred.

TABLE 1

Compounds of the general formula (I) according to the invention, where A is A1, R$^6$ is methyl, R is CH(Me)OCO$_2$Et, W is CY and V is hydrogen

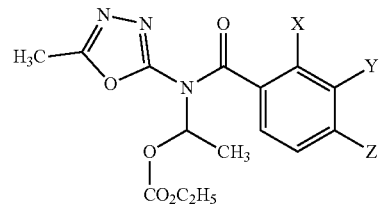

| No. | X | Y | Z | Physical data ($^1$H NMR (400 MHz; CDCl$_3$): |
|---|---|---|---|---|
| 1-1 | F | H | Cl | |
| 1-2 | F | H | SO$_2$Me | |
| 1-3 | F | H | SO$_2$Et | |
| 1-4 | F | H | CF$_3$ | |
| 1-5 | F | H | NO$_2$ | |
| 1-6 | Cl | H | Br | |
| 1-7 | Cl | H | SMe | |
| 1-8 | Cl | H | SOMe | |
| 1-9 | Cl | H | SO$_2$Me | |
| 1-10 | Cl | H | SO$_2$CH$_2$Cl | |
| 1-11 | Cl | H | SEt | |
| 1-12 | Cl | H | SO$_2$Et | |
| 1-13 | Cl | H | CF$_3$ | |
| 1-14 | Cl | H | NO$_2$ | |
| 1-15 | Cl | H | pyrazol-1-yl | |
| 1-16 | Cl | H | 1H-1,2,4-triazol-1-yl | |
| 1-17 | Br | H | Cl | |
| 1-18 | Br | H | Br | |
| 1-19 | Br | H | SO$_2$Me | |
| 1-20 | Br | H | SO$_2$Et | |
| 1-21 | Br | H | CF$_3$ | |
| 1-22 | SO$_2$Me | H | Cl | |
| 1-23 | SO$_2$Me | H | Br | |
| 1-24 | SO$_2$Me | H | SMe | |
| 1-25 | SO$_2$Me | H | SOMe | |
| 1-26 | SO$_2$Me | H | SO$_2$Me | |
| 1-27 | SO$_2$Me | H | SO$_2$Et | |
| 1-28 | SO$_2$Me | H | CF$_3$ | |
| 1-29 | SO$_2$Et | H | Cl | |
| 1-30 | SO$_2$Et | H | Br | |
| 1-31 | SO$_2$Et | H | SMe | |
| 1-32 | SO$_2$Et | H | SOMe | |
| 1-33 | SO$_2$Et | H | SO$_2$Me | |
| 1-34 | SO$_2$Et | H | CF$_3$ | |
| 1-35 | NO$_2$ | H | F | |
| 1-36 | NO$_2$ | H | Cl | |
| 1-37 | NO$_2$ | H | Br | |
| 1-38 | NO$_2$ | H | I | |

TABLE 1-continued

Compounds of the general formula (I) according to the invention, where A is A1, $R^6$ is methyl, R is CH(Me)OCO$_2$Et, W is CY and V is hydrogen

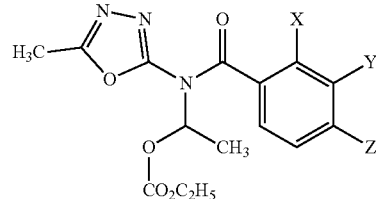

| No. | X | Y | Z | Physical data ($^1$H NMR (400 MHz; CDCl$_3$): |
|---|---|---|---|---|
| 1-39 | NO$_2$ | H | CN | |
| 1-40 | NO$_2$ | H | SO$_2$Me | |
| 1-41 | NO$_2$ | H | SO$_2$Et | |
| 1-42 | NO$_2$ | H | CF$_3$ | |
| 1-43 | Me | H | Cl | |
| 1-44 | Me | H | Br | |
| 1-45 | Me | H | SMe | |
| 1-46 | Me | H | SO$_2$Me | |
| 1-47 | Me | H | SO$_2$CH$_2$Cl | |
| 1-48 | Me | H | SEt | |
| 1-49 | Me | H | SO$_2$Et | |
| 1-50 | Me | H | CF$_3$ | |
| 1-51 | CH$_2$SO$_2$Me | H | CF$_3$ | |
| 1-52 | Et | H | Cl | |
| 1-53 | Et | H | Br | |
| 1-54 | Et | H | SMe | |
| 1-55 | Et | H | SO$_2$Me | |
| 1-56 | Et | H | SO$_2$CH$_2$Cl | |
| 1-57 | Et | H | SEt | |
| 1-58 | Et | H | SO$_2$Et | |
| 1-59 | Et | H | CF$_3$ | |
| 1-60 | CF$_3$ | H | Cl | |
| 1-61 | CF$_3$ | H | Br | |
| 1-62 | CF$_3$ | H | SO$_2$Me | |
| 1-63 | CF$_3$ | H | SO$_2$Et | |
| 1-64 | CF$_3$ | H | CF$_3$ | |
| 1-65 | NO$_2$ | NH$_2$ | F | |
| 1-66 | NO$_2$ | NHMe | F | |
| 1-67 | NO$_2$ | NMe$_2$ | F | |
| 1-68 | NO$_2$ | Me | Cl | |
| 1-69 | NO$_2$ | NH$_2$ | Cl | |
| 1-70 | NO$_2$ | NHMe | Cl | |
| 1-71 | NO$_2$ | NMe$_2$ | Cl | |
| 1-72 | NO$_2$ | NH$_2$ | Br | |
| 1-73 | NO$_2$ | NHMe | Br | |
| 1-74 | NO$_2$ | NMe$_2$ | Br | |
| 1-75 | NO$_2$ | NH$_2$ | CF$_3$ | |
| 1-76 | NO$_2$ | NMe$_2$ | CF$_3$ | |
| 1-77 | NO$_2$ | NH$_2$ | SO$_2$Me | |
| 1-78 | NO$_2$ | NH$_2$ | SO$_2$Et | |
| 1-79 | NO$_2$ | NHMe | SO$_2$Me | |
| 1-80 | NO$_2$ | NMe$_2$ | SO$_2$Me | |
| 1-81 | NO$_2$ | NMe$_2$ | SO$_2$Et | |
| 1-82 | NO$_2$ | NH$_2$ | 1H-1,2,4-triazol-1-yl | |
| 1-83 | NO$_2$ | NHMe | 1H-1,2,4-triazol-1-yl | |
| 1-84 | NO$_2$ | NMe$_2$ | 1H-1,2,4-triazol-1-yl | |
| 1-85 | Me | SMe | H | |
| 1-86 | Me | SOMe | H | |
| 1-87 | Me | SO$_2$Me | H | |
| 1-88 | Me | SEt | H | |
| 1-89 | Me | SOEt | H | |
| 1-90 | Me | SO$_2$Et | H | |
| 1-91 | Me | S(CH$_2$)$_2$OMe | H | |
| 1-92 | Me | SO(CH$_2$)$_2$OMe | H | |
| 1-93 | Me | SO$_2$(CH$_2$)$_2$OMe | H | |
| 1-94 | Me | F | F | |
| 1-95 | Me | F | Cl | |
| 1-96 | Me | SEt | F | |
| 1-97 | Me | SOEt | F | |
| 1-98 | Me | SO$_2$Et | F | |
| 1-99 | Me | Me | Cl | |
| 1-100 | Me | F | Cl | |
| 1-101 | Me | Cl | Cl | |

TABLE 1-continued

Compounds of the general formula (I) according to the invention, where A is A1, $R^6$ is methyl, R is $CH(Me)OCO_2Et$, W is CY and V is hydrogen

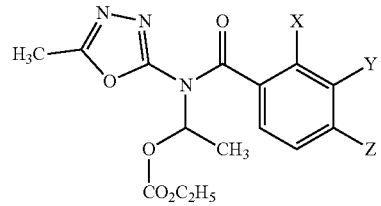

| No. | X | Y | Z | Physical data ($^1$H NMR (400 MHz; CDCl$_3$): |
|---|---|---|---|---|
| 1-102 | Me | NH$_2$ | Cl | |
| 1-103 | Me | NHMe | Cl | |
| 1-104 | Me | NMe$_2$ | Cl | |
| 1-105 | Me | O(CH$_2$)$_2$OMe | Cl | |
| 1-106 | Me | O(CH$_2$)$_3$OMe | Cl | |
| 1-107 | Me | O(CH$_2$)$_4$OMe | Cl | |
| 1-108 | Me | OCH$_2$CONMe$_2$ | Cl | |
| 1-109 | Me | O(CH$_2$)$_2$—CO—NMe$_2$ | Cl | |
| 1-110 | Me | O(CH$_2$)$_2$—NH(CO)NMe$_2$ | Cl | |
| 1-111 | Me | O(CH$_2$)$_2$—NH(CO)NHCO$_2$Et | Cl | |
| 1-112 | Me | O(CH$_2$)$_2$—NHCO$_2$Me | Cl | |
| 1-113 | Me | OCH$_2$—NHSO$_2$cPr | Cl | |
| 1-114 | Me | O(CH$_2$)-5-2,4-dimethyl-2,4-dihydro-3H-1,2,4-triazol-3-one | Cl | |
| 1-115 | Me | O(CH$_2$)-3,5-dimethyl-1,2-oxazol-4-yl | Cl | |
| 1-116 | Me | SMe | Cl | |
| 1-117 | Me | SOMe | Cl | |
| 1-118 | Me | SO$_2$Me | Cl | |
| 1-119 | Me | SEt | Cl | |
| 1-120 | Me | SOEt | Cl | |
| 1-121 | Me | SO$_2$Et | Cl | |
| 1-122 | Me | S(CH$_2$)$_2$OMe | Cl | |
| 1-123 | Me | SO(CH$_2$)$_2$OMe | Cl | |
| 1-124 | Me | SO$_2$(CH$_2$)$_2$OMe | Cl | |
| 1-125 | Me | NH$_2$ | Br | |
| 1-126 | Me | NHMe | Br | |
| 1-127 | Me | NMe$_2$ | Br | |
| 1-128 | Me | OCH$_2$(CO)NMe$_2$ | Br | |
| 1-129 | Me | O(CH$_2$)-5-pyrrolidin-2-one | Br | |
| 1-130 | Me | SMe | Br | |
| 1-131 | Me | SOMe | Br | |
| 1-132 | Me | SO$_2$Me | Br | |
| 1-133 | Me | SEt | Br | |
| 1-134 | Me | SOEt | Br | |
| 1-135 | Me | SO$_2$Et | Br | |
| 1-136 | Me | SMe | I | |
| 1-137 | Me | SOMe | I | |
| 1-138 | Me | SO$_2$Me | I | |
| 1-139 | Me | SEt | I | |
| 1-140 | Me | SOEt | I | |
| 1-141 | Me | SO$_2$Et | I | |
| 1-142 | Me | Cl | CF$_3$ | |
| 1-143 | Me | SMe | CF$_3$ | |
| 1-144 | Me | SOMe | CF$_3$ | |
| 1-145 | Me | SO$_2$Me | CF$_3$ | 7.73 ppm (d, 1H); 7.53 ppm (d, 1H), 7.05-6.92 (broad, 1H), 4.32-4.26 (m, 2H); 3.21 (s, 3H); 2.80 (s, 3H), 2.43 (s, 3H), 1.62 (d, 3H), 1.36 (t, 3H) |
| 1-146 | Me | SEt | CF$_3$ | |
| 1-147 | Me | SOEt | CF$_3$ | |
| 1-148 | Me | SO$_2$Et | CF$_3$ | |
| 1-149 | Me | S(CH$_2$)$_2$OMe | CF$_3$ | |
| 1-150 | Me | SO(CH$_2$)$_2$OMe | CF$_3$ | |
| 1-151 | Me | SO$_2$(CH$_2$)$_2$OMe | CF$_3$ | |
| 1-152 | Me | Me | SO$_2$Me | |
| 1-153 | Me | 4,5-dihydro-1,2-oxazol-3-yl | SO$_2$Me | |
| 1-154 | Me | 4,5-dihydro-1,2-oxazol-3-yl | SO$_2$Et | |
| 1-155 | Me | 5-cyanomethyl-4,5-dihydro-1,2-oxazol-3-yl | SO$_2$Me | |

TABLE 1-continued

Compounds of the general formula (I) according to the invention, where A is A1, $R^6$ is methyl, R is $CH(Me)OCO_2Et$, W is CY and V is hydrogen

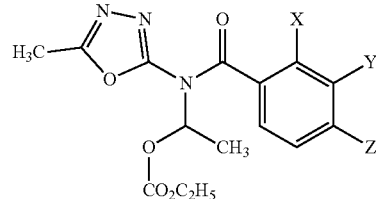

| No. | X | Y | Z | Physical data ($^1$H NMR (400 MHz; CDCl$_3$)): |
|---|---|---|---|---|
| 1-156 | Me | 5-cyanomethyl-4,5-dihydro-1,2-oxazol-3-yl | SO$_2$Et | |
| 1-157 | Me | NH$_2$ | SO$_2$Me | |
| 1-158 | Me | NHMe | SO$_2$Me | |
| 1-159 | Me | NMe$_2$ | SO$_2$Me | |
| 1-160 | Me | NH(CH$_2$)$_2$OMe | SO$_2$Me | |
| 1-161 | Me | pyrazol-1-yl | SO$_2$Me | |
| 1-162 | Me | OH | SO$_2$Me | |
| 1-163 | Me | OMe | SO$_2$Me | |
| 1-164 | Me | OMe | SO$_2$Et | |
| 1-165 | Me | OEt | SO$_2$Me | |
| 1-166 | Me | OEt | SO$_2$Et | |
| 1-167 | Me | OiPr | SO$_2$Me | |
| 1-168 | Me | OiPr | SO$_2$Et | |
| 1-169 | Me | O(CH$_2$)$_2$OMe | SO$_2$Me | |
| 1-170 | Me | O(CH$_2$)$_2$OMe | SO$_2$Et | |
| 1-171 | Me | O(CH$_2$)$_3$OMe | SO$_2$Me | |
| 1-172 | Me | O(CH$_2$)$_3$OMe | SO$_2$Et | |
| 1-173 | Me | O(CH$_2$)$_4$OMe | SO$_2$Me | |
| 1-174 | Me | O(CH$_2$)$_4$OMe | SO$_2$Et | |
| 1-175 | Me | O(CH$_2$)$_2$NHSO$_2$Me | SO$_2$Me | |
| 1-176 | Me | O(CH$_2$)$_2$NHSO$_2$Me | SO$_2$Et | |
| 1-177 | Me | OCH$_2$(CO)NMe$_2$ | SO$_2$Me | |
| 1-178 | Me | OCH$_2$(CO)NMe$_2$ | SO$_2$Et | |
| 1-179 | Me | [1,4]dioxan-2-ylmethoxy | SO$_2$Me | |
| 1-180 | Me | [1,4]dioxan-2-ylmethoxy | SO$_2$Et | |
| 1-181 | Me | O(CH$_2$)$_2$-O-(3,5-dimethoxypyrimidin-2-yl) | SO$_2$Me | |
| 1-182 | Me | Cl | SO$_2$Me | |
| 1-183 | Me | SMe | SO$_2$Me | |
| 1-184 | Me | SOMe | SO$_2$Me | |
| 1-185 | Me | SO$_2$Me | SO$_2$Me | |
| 1-186 | Me | SO$_2$Me | SO$_2$Et | |
| 1-187 | Me | SEt | SO$_2$Me | |
| 1-188 | Me | SOEt | SO$_2$Me | |
| 1-189 | Me | SO$_2$Et | SO$_2$Me | |
| 1-190 | Me | S(CH$_2$)$_2$OMe | SO$_2$Me | |
| 1-191 | Me | SO(CH$_2$)$_2$OMe | SO$_2$Me | |
| 1-192 | Me | SO$_2$(CH$_2$)$_2$OMe | SO$_2$Me | |
| 1-193 | CH$_2$SMe | OMe | SO$_2$Me | |
| 1-194 | CH$_2$OMe | OMe | SO$_2$Me | |
| 1-195 | CH$_2$O(CH$_2$)$_2$OMe | NH(CH$_2$)$_2$OEt | SO$_2$Me | |
| 1-196 | CH$_2$O(CH$_2$)$_2$OMe | NH(CH$_2$)$_3$OEt | SO$_2$Me | |
| 1-197 | CH$_2$O(CH$_2$)$_3$OMe | OMe | SO$_2$Me | |
| 1-198 | CH$_2$O(CH$_2$)$_2$OMe | NH(CH$_2$)$_2$OMe | SO$_2$Me | |
| 1-199 | CH$_2$O(CH$_2$)$_2$OMe | NH(CH$_2$)$_3$OMe | SO$_2$Me | |
| 1-200 | Et | SMe | Cl | |
| 1-201 | Et | SO$_2$Me | Cl | |
| 1-202 | Et | SMe | CF$_3$ | |
| 1-203 | Et | SO$_2$Me | CF$_3$ | |
| 1-204 | Et | F | SO$_2$Me | |
| 1-205 | Et | NH(CH$_2$)$_2$OMe | SO$_2$Me | |
| 1-206 | iPr | SO$_2$Me | CF$_3$ | |
| 1-207 | cPr | SO$_2$Me | CF$_3$ | |
| 1-208 | CF$_3$ | O(CH$_2$)$_2$OMe | F | |
| 1-209 | CF$_3$ | O(CH$_2$)$_3$OMe | F | |
| 1-210 | CF$_3$ | OCH$_2$CONMe$_2$ | F | |
| 1-211 | CF$_3$ | [1,4]dioxan-2-yl-methoxy | F | |
| 1-212 | CF$_3$ | O(CH$_2$)$_2$OMe | Cl | |
| 1-213 | CF$_3$ | O(CH$_2$)$_3$OMe | Cl | |
| 1-214 | CF$_3$ | OCH$_2$CONMe$_2$ | Cl | |
| 1-215 | CF$_3$ | [1,4]dioxan-2-yl-methoxy | Cl | |
| 1-216 | CF$_3$ | O(CH$_2$)$_2$OMe | Br | |

TABLE 1-continued

Compounds of the general formula (I) according to the invention, where A is A1, $R^6$ is methyl, R is CH(Me)OCO$_2$Et, W is CY and V is hydrogen

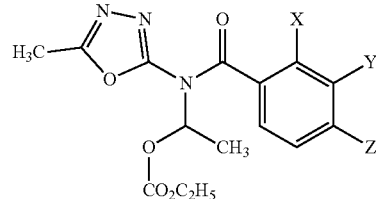

| No. | X | Y | Z | Physical data ($^1$H NMR (400 MHz; CDCl$_3$)): |
|---|---|---|---|---|
| 1-217 | CF$_3$ | O(CH$_2$)$_3$OMe | Br | |
| 1-218 | CF$_3$ | OCH$_2$CONMe$_2$ | Br | |
| 1-219 | CF$_3$ | [1,4]dioxan-2-yl-methoxy | Br | |
| 1-220 | CF$_3$ | O(CH$_2$)$_2$OMe | I | |
| 1-221 | CF$_3$ | O(CH$_2$)$_3$OMe | I | |
| 1-222 | CF$_3$ | OCH$_2$CONMe$_2$ | I | |
| 1-223 | CF$_3$ | [1,4]dioxan-2-ylmethoxy | I | |
| 1-224 | CF$_3$ | F | SO$_2$Me | |
| 1-225 | CF$_3$ | F | SO$_2$Et | |
| 1-226 | CF$_3$ | O(CH$_2$)$_2$OMe | SO$_2$Me | |
| 1-227 | CF$_3$ | O(CH$_2$)$_2$OMe | SO$_2$Et | |
| 1-228 | CF$_3$ | O(CH$_2$)$_3$OMe | SO$_2$Me | |
| 1-229 | CF$_3$ | O(CH$_2$)$_3$OMe | SO$_2$Et | |
| 1-230 | CF$_3$ | OCH$_2$CONMe$_2$ | SO$_2$Me | |
| 1-231 | CF$_3$ | OCH$_2$CONMe$_2$ | SO$_2$Et | |
| 1-232 | CF$_3$ | [1,4]dioxan-2-ylmethoxy | SO$_2$Me | |
| 1-233 | CF$_3$ | [1,4]dioxan-2-ylmethoxy | SO$_2$Et | |
| 1-234 | F | SMe | CF$_3$ | |
| 1-235 | F | SOMe | CF$_3$ | |
| 1-236 | Cl | Me | Cl | |
| 1-237 | Cl | OCH$_2$CHCH$_2$ | Cl | |
| 1-238 | Cl | OCH$_2$CHF$_2$ | Cl | |
| 1-239 | Cl | O(CH$_2$)$_2$OMe | Cl | |
| 1-240 | Cl | OCH$_2$CONMe$_2$ | Cl | |
| 1-241 | Cl | O(CH$_2$)-5-pyrrolidin-2-one | Cl | |
| 1-242 | Cl | SMe | Cl | |
| 1-243 | Cl | SOMe | Cl | |
| 1-244 | Cl | SO$_2$Me | Cl | |
| 1-245 | Cl | F | SMe | |
| 1-246 | Cl | Cl | SO$_2$Me | |
| 1-247 | Cl | CO$_2$Me | SO$_2$Me | |
| 1-248 | Cl | CONMe$_2$ | SO$_2$Me | |
| 1-249 | Cl | CONMe(OMe) | SO$_2$Me | |
| 1-250 | Cl | CH$_2$OMe | SO$_2$Me | |
| 1-251 | Cl | CH$_2$OMe | SO$_2$Et | |
| 1-252 | Cl | CH$_2$OEt | SO$_2$Me | |
| 1-253 | Cl | CH$_2$OEt | SO$_2$Et | |
| 1-254 | Cl | CH$_2$OCH$_2$CHF$_2$ | SO$_2$Me | |
| 1-255 | Cl | CH$_2$OCH$_2$CF$_3$ | SO$_2$Me | |
| 1-256 | Cl | CH$_2$OCH$_2$CF$_3$ | SO$_2$Et | |
| 1-257 | Cl | CH$_2$OCH$_2$CF$_2$CHF$_2$ | SO$_2$Me | |
| 1-258 | Cl | CH$_2$OcPentyl | SO$_2$Me | |
| 1-259 | Cl | CH$_2$PO(OMe)$_2$ | SO$_2$Me | |
| 1-260 | Cl | 4,5-dihydro-1,2-oxazol-3-yl | SMe | |
| 1-261 | Cl | 4,5-dihydro-1,2-oxazol-3-yl | SO$_2$Me | |
| 1-262 | Cl | 4,5-dihydro-1,2-oxazol-3-yl | SO$_2$Et | |
| 1-263 | Cl | 5-cyanomethyl- 4,5-dihydro-1,2-oxazol-3-yl | SO$_2$Me | |
| 1-264 | Cl | 5-cyanomethyl-4,5-dihydro-1,2-oxazol-3-yl | SO$_2$Et | |
| 1-265 | Cl | 5-(methoxymethyl)-4,5-dihydro-1,2-oxazol-3-yl | SO$_2$Et | |
| 1-266 | Cl | 5-(methoxymethyl)-5-methyl-4,5-dihydro-1,2-oxazol-3-yl | SO$_2$Et | |
| 1-267 | Cl | CH$_2$O-tetrahydrofuran-3-yl | SO$_2$Me | |
| 1-268 | Cl | CH$_2$O-tetrahydrofuran-3-yl | SO$_2$Et | |
| 1-269 | Cl | CH$_2$OCH$_2$-tetrahydrofuran-2-yl | SO$_2$Me | |
| 1-270 | Cl | CH$_2$OCH$_2$-tetrahydrofuran-2-yl | SO$_2$Et | |

TABLE 1-continued

Compounds of the general formula (I) according to the invention, where A is A1, $R^6$ is methyl, R is CH(Me)OCO$_2$Et, W is CY and V is hydrogen

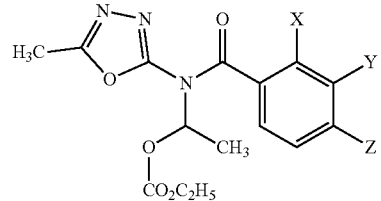

| No. | X | Y | Z | Physical data ($^1$H NMR (400 MHz; CDCl$_3$): |
|---|---|---|---|---|
| 1-271 | Cl | CH$_2$OCH$_2$-tetrahydrofuran-3-yl | SO$_2$Me | |
| 1-272 | Cl | CH$_2$OCH$_2$-tetrahydrofuran-3-yl | SO$_2$Et | |
| 1-273 | Cl | OMe | SO$_2$Me | |
| 1-274 | Cl | OMe | SO$_2$Et | |
| 1-275 | Cl | OEt | SO$_2$Me | |
| 1-276 | Cl | OEt | SO$_2$Et | |
| 1-277 | Cl | OiPr | SO$_2$Me | |
| 1-278 | Cl | OiPr | SO$_2$Et | |
| 1-279 | Cl | O(CH$_2$)$_2$OMe | SO$_2$Me | |
| 1-280 | Cl | O(CH$_2$)$_4$OMe | SO$_2$Me | |
| 1-281 | Cl | O(CH$_2$)$_4$OMe | SO$_2$Et | |
| 1-282 | Cl | O(CH$_2$)$_3$OMe | SO$_2$Me | |
| 1-283 | Cl | O(CH$_2$)$_3$OMe | SO$_2$Et | |
| 1-284 | Cl | O(CH$_2$)$_2$OMe | SO$_2$Me | |
| 1-285 | Cl | O(CH$_2$)$_2$OMe | SO$_2$Et | |
| 1-286 | Cl | [1,4]dioxan-2-ylmethoxy | SO$_2$Me | |
| 1-287 | Cl | [1,4]dioxan-2-ylmethoxy | SO$_2$Et | |
| 1-288 | Cl | OCH$_2$(CO)NMe$_2$ | SO$_2$Me | |
| 1-289 | Cl | OCH$_2$(CO)NMe$_2$ | SO$_2$Et | |
| 1-290 | Cl | SMe | SO$_2$Me | |
| 1-291 | Cl | SOMe | SO$_2$Me | |
| 1-292 | Br | OMe | Br | |
| 1-293 | Br | O(CH$_2$)$_2$OMe | Br | |
| 1-294 | Br | O(CH$_2$)$_2$OMe | SO$_2$Me | |
| 1-295 | Br | O(CH$_2$)$_2$OMe | SO$_2$Et | |
| 1-296 | Br | O(CH$_2$)$_3$OMe | SO$_2$Me | |
| 1-297 | Br | O(CH$_2$)$_3$OMe | SO$_2$Et | |
| 1-298 | Br | O(CH$_2$)$_4$OMe | SO$_2$Me | |
| 1-299 | Br | O(CH$_2$)$_4$OMe | SO$_2$Et | |
| 1-300 | Br | [1,4]dioxan-2-ylmethoxy | SO$_2$Me | |
| 1-301 | Br | [1,4]dioxan-2-ylmethoxy | SO$_2$Et | |
| 1-302 | I | O(CH$_2$)$_2$OMe | SO$_2$Me | |
| 1-303 | I | O(CH$_2$)$_2$OMe | SO$_2$Et | |
| 1-304 | I | O(CH$_2$)$_3$OMe | SO$_2$Me | |
| 1-305 | I | O(CH$_2$)$_3$OMe | SO$_2$Et | |
| 1-306 | I | O(CH$_2$)$_4$OMe | SO$_2$Me | |
| 1-307 | I | O(CH$_2$)$_4$OMe | SO$_2$Et | |
| 1-308 | I | [1,4]dioxan-2-ylmethoxy | SO$_2$Me | |
| 1-309 | I | [1,4]dioxan-2-ylmethoxy | SO$_2$Et | |
| 1-310 | OMe | SMe | CF$_3$ | |
| 1-311 | OMe | SOMe | CF$_3$ | |
| 1-312 | OMe | SO$_2$Me | CF$_3$ | |
| 1-313 | OMe | SOEt | CF$_3$ | |
| 1-314 | OMe | SO$_2$Et | CF$_3$ | |
| 1-315 | OMe | S(CH$_2$)$_2$OMe | CF$_3$ | |
| 1-316 | OMe | SO(CH$_2$)$_2$OMe | CF$_3$ | |
| 1-317 | OMe | SO$_2$(CH$_2$)$_2$OMe | CF$_3$ | |
| 1-318 | OMe | SMe | Cl | |
| 1-319 | OMe | SOMe | Cl | |
| 1-320 | OMe | SO$_2$Me | Cl | |
| 1-321 | OMe | SEt | Cl | |
| 1-322 | OMe | SOEt | Cl | |
| 1-323 | OMe | SO$_2$Et | Cl | |
| 1-324 | OMe | S(CH$_2$)$_2$OMe | Cl | |
| 1-325 | OMe | SO(CH$_2$)$_2$OMe | Cl | |
| 1-326 | OMe | SO$_2$(CH$_2$)$_2$OMe | Cl | |
| 1-327 | OCH$_2$-c-Pr | SMe | CF$_3$ | |
| 1-328 | OCH$_2$-c-Pr | SOMe | CF$_3$ | |
| 1-329 | OCH$_2$-c-Pr | SO$_2$Me | CF$_3$ | |
| 1-330 | OCH$_2$-c-Pr | SEt | CF$_3$ | |
| 1-331 | OCH$_2$-c-Pr | SOEt | CF$_3$ | |

TABLE 1-continued

Compounds of the general formula (I) according to the invention, where A is A1, $R^6$ is methyl, R is $CH(Me)OCO_2Et$, W is CY and V is hydrogen

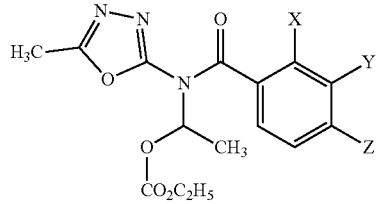

| No. | X | Y | Z | Physical data ($^1$H NMR (400 MHz; CDCl$_3$): |
|---|---|---|---|---|
| 1-332 | OCH$_2$-c-Pr | SO$_2$Et | CF$_3$ | |
| 1-333 | OCH$_2$-c-Pr | S(CH$_2$)$_2$OMe | CF$_3$ | |
| 1-334 | OCH$_2$-c-Pr | SO(CH$_2$)$_2$OMe | CF$_3$ | |
| 1-335 | OCH$_2$-c-Pr | SO$_2$(CH$_2$)$_2$OMe | CF$_3$ | |
| 1-336 | OCH$_2$-c-Pr | SMe | Cl | |
| 1-337 | OCH$_2$-c-Pr | SOMe | Cl | |
| 1-338 | OCH$_2$-c-Pr | SO$_2$Me | Cl | |
| 1-339 | OCH$_2$-c-Pr | SEt | Cl | |
| 1-340 | OCH$_2$-c-Pr | SOEt | Cl | |
| 1-341 | OCH$_2$-c-Pr | SO$_2$Et | Cl | |
| 1-342 | OCH$_2$-c-Pr | S(CH$_2$)$_2$OMe | Cl | |
| 1-343 | OCH$_2$-c-Pr | SO(CH$_2$)$_2$OMe | Cl | |
| 1-344 | OCH$_2$-c-Pr | SO$_2$(CH$_2$)$_2$OMe | Cl | |
| 1-345 | OCH$_2$-c-Pr | SMe | SO$_2$Me | |
| 1-346 | OCH$_2$-c-Pr | SOMe | SO$_2$Me | |
| 1-347 | OCH$_2$-c-Pr | SO$_2$Me | SO$_2$Me | |
| 1-348 | OCH$_2$-c-Pr | SEt | SO$_2$Me | |
| 1-349 | OCH$_2$-c-Pr | SOEt | SO$_2$Me | |
| 1-350 | OCH$_2$-c-Pr | SO$_2$Et | SO$_2$Me | |
| 1-351 | OCH$_2$-c-Pr | S(CH$_2$)$_2$OMe | SO$_2$Me | |
| 1-352 | OCH$_2$-c-Pr | SO(CH$_2$)$_2$OMe | SO$_2$Me | |
| 1-353 | OCH$_2$-c-Pr | SO$_2$(CH$_2$)$_2$OMe | SO$_2$Me | |
| 1-354 | SO$_2$Me | F | CF$_3$ | |
| 1-355 | SO$_2$Me | NH$_2$ | CF$_3$ | |
| 1-356 | SO$_2$Me | NHEt | Cl | |
| 1-357 | SMe | SEt | F | |
| 1-358 | SMe | SMe | F | |
| 1-359 | SMe | SMe | CF$_3$ | |
| 1-360 | SMe | SOMe | CF$_3$ | |
| 1-361 | SMe | SO$_2$Me | CF$_3$ | |
| 1-362 | SMe | SMe | Cl | |
| 1-363 | SMe | SMe | Br | |
| 1-364 | Cl | Ac | CF$_3$ | |
| 1-365 | Cl | Ac | SO$_2$Me | |
| 1-366 | Cl | C(O)cPr | CF$_3$ | |
| 1-367 | Cl | C(O)cPr | SO$_2$Me | |
| 1-368 | Cl | CH$_2$SMe | CF$_3$ | |
| 1-369 | Cl | CH$_2$S(O)Me | CF$_3$ | |
| 1-370 | Cl | CH$_2$SO$_2$Me | CF$_3$ | |
| 1-371 | Cl | CH$_2$SMe | SO$_2$Me | |
| 1-372 | Cl | CH$_2$S(O)Me | SO$_2$Me | |
| 1-373 | Cl | CH$_2$SO$_2$Me | SO$_2$Me | |
| 1-374 | Cl | CH=NOMe | CF$_3$ | |
| 1-375 | Cl | CH=NOMe | SO$_2$Me | |
| 1-376 | Cl | 4,5-dihydro-1,2-oxazol-5-yl | CF$_3$ | |
| 1-377 | Cl | 4,5-dihydro-1,2-oxazol-5-yl | SO$_2$Me | |
| 1-378 | Cl | 3-methyl-4,5-dihydro-1,2-oxazol-5-yl | CF$_3$ | |
| 1-379 | Cl | 3-methyl-4,5-dihydro-1,2-oxazol-5-yl | SO$_2$Me | |
| 1-380 | Cl | vinyl | CF$_3$ | |
| 1-381 | Cl | vinyl | SO$_2$Me | |
| 1-382 | Cl | CO$_2$Me | CF$_3$ | |
| 1-383 | Cl | CO$_2$Me | SO$_2$Me | |
| 1-384 | Cl | SMe | CF$_3$ | |
| 1-385 | Cl | S(O)Me | CF$_3$ | 7.70 ppm (d, 1H); 7.63 ppm (d, 1H), 7.12-6.91 (broad, 1H), 4.28 (q, 2H); 3.07 and 3.05 (2s, 3H); 2.46 (s, 3H), 1.66 and 1.64 (2d, 3H), 1.34 (t, 3H) |
| 1-386 | Cl | SO$_2$Me | CF$_3$ | |
| 1-387 | Cl | SO$_2$Me | SO$_2$Me | |
| 1-388 | Cl | SMe | Me | |

TABLE 1-continued

Compounds of the general formula (I) according to the invention, where A is A1, $R^6$ is methyl, R is CH(Me)OCO$_2$Et, W is CY and V is hydrogen

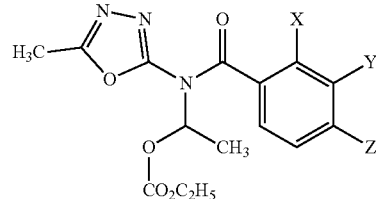

| No. | X | Y | Z | Physical data ($^1$H NMR (400 MHz; CDCl$_3$)): |
|---|---|---|---|---|
| 1-389 | Cl | SOMe | Me | |
| 1-390 | Cl | SO$_2$Me | Me | |
| 1-391 | Cl | 1H-1,2,4-triazol-1-yl | CF$_3$ | |
| 1-392 | Cl | 1H-1,2,3-triazol-1-yl | CF$_3$ | |
| 1-393 | Cl | 2H-1,2,3-triazol-2-yl | CF$_3$ | |
| 1-394 | Cl | 1H-pyrazol-1-yl | CF$_3$ | |
| 1-395 | Cl | 1H-4-chloropyrazol-1-yl | CF$_3$ | |
| 1-396 | Cl | 1H-3-bromopyrazol-1-yl | CF$_3$ | |
| 1-397 | Cl | 1H-4-trifluoromethyl-pyrazol-1-yl | CF$_3$ | |
| 1-398 | Cl | pyrolidin-2-on-1-yl | CF$_3$ | |
| 1-399 | Cl | morpholin-3-on-4-yl | CF$_3$ | |
| 1-400 | Cl | 1,2-thiazolidine-1,1-dioxid-2-yl | CF$_3$ | |
| 1-401 | Br | 1H-1,2,4-triazol-1-yl | CF$_3$ | |
| 1-402 | Br | 1H-1,2,3-triazol-1-yl | CF$_3$ | |
| 1-403 | Br | 2H-1,2,3-triazol-2-yl | CF$_3$ | |
| 1-404 | Br | 1H-pyrazol-1-yl | CF$_3$ | |
| 1-405 | Br | 1H-4-chloropyrazol-1-yl | CF$_3$ | |
| 1-406 | Br | 1H-3-bromopyrazol-1-yl | CF$_3$ | |
| 1-407 | Br | 1H-4-trifluoromethyl-pyrazol-1-yl | CF$_3$ | |
| 1-408 | Br | pyrolidin-2-on-1-yl | CF$_3$ | |
| 1-409 | Br | morpholin-3-on-4-yl | CF$_3$ | |
| 1-410 | Br | 1,2-thiazolidine-1,1-dioxid-2-yl | CF$_3$ | |
| 1-411 | CH$_2$OMe | 1H-1,2,4-triazol-1-yl | CF$_3$ | |
| 1-412 | CH$_2$OMe | 1H-1,2,3-triazol-1-yl | CF$_3$ | |
| 1-413 | CH$_2$OMe | 2H-1,2,3-triazol-2-yl | CF$_3$ | |
| 1-414 | CF$_3$ | OCH$_2$CH$_2$F | CF$_3$ | |
| 1-415 | CF$_3$ | OMe | CF$_3$ | |
| 1-416 | CF$_3$ | SMe | CF$_3$ | |
| 1-417 | CF$_3$ | SOMe | CF$_3$ | |
| 1-418 | CF$_3$ | SO$_2$Me | CF$_3$ | |
| 1-419 | CF$_3$ | 1H-pyrazol-1-yl | CF$_3$ | |
| 1-420 | Me | SMe | Et | |
| 1-421 | Me | SOMe | Et | |
| 1-422 | Me | SO$_2$Me | Et | |
| 1-423 | Me | 1H-pyrazol-1-yl | Et | |
| 1-424 | Me | OCH$_2$CH$_2$F | Et | |
| 1-425 | Me | OMe | Et | |
| 1-426 | Me | Ac | CF$_3$ | |
| 1-427 | Me | Ac | SO$_2$Me | |
| 1-428 | Me | C(O)cPr | CF$_3$ | |
| 1-429 | Me | C(O)cPr | SO$_2$Me | |
| 1-430 | Me | CH$_2$SMe | CF$_3$ | |
| 1-431 | Me | CH$_2$S(O)Me | CF$_3$ | |
| 1-432 | Me | CH$_2$SO$_2$Me | CF$_3$ | |
| 1-433 | Me | CH$_2$SMe | SO$_2$Me | |
| 1-434 | Me | CH$_2$S(O)Me | SO$_2$Me | |
| 1-435 | Me | CH$_2$SO$_2$Me | SO$_2$Me | |
| 1-436 | Me | CH=NOMe | CF$_3$ | |
| 1-437 | Me | CH=NOMe | SO$_2$Me | |
| 1-438 | Me | 4,5-dihydro-1,2-oxazol-5-yl, | CF$_3$ | |
| 1-439 | Me | 4,5-dihydro-1,2-oxazol-5-yl | SO$_2$Me | |
| 1-440 | Me | 3-methyl-4,5-dihydro-1,2-oxazol-5-yl | CF$_3$ | |
| 1-441 | Me | 3-methyl-4,5-dihydro-1,2-oxazol-5-yl | SO$_2$Me | |
| 1-442 | Me | vinyl | CF$_3$ | |
| 1-443 | Me | vinyl | SO$_2$Me | |
| 1-444 | Me | CO$_2$Me | CF$_3$ | |
| 1-445 | Me | CO$_2$Me | SO$_2$Me | |

TABLE 1-continued

Compounds of the general formula (I) according to the invention, where A is A1, $R^6$ is methyl, R is CH(Me)OCO$_2$Et, W is CY and V is hydrogen

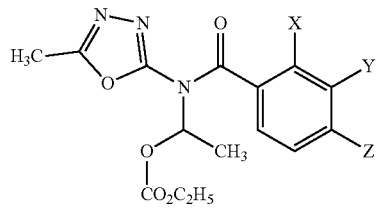

| No. | X | Y | Z | Physical data ($^1$H NMR (400 MHz; CDCl$_3$)): |
|---|---|---|---|---|
| 1-446 | Cl | SMe | CF$_3$ | |
| 1-447 | Cl | SOMe | CF$_3$ | |
| 1-448 | Cl | SO$_2$Me | CF$_3$ | |
| 1-449 | Et | SEt | CF$_3$ | |
| 1-450 | Et | SOEt | CF$_3$ | |
| 1-451 | Et | SO$_2$Et | CF$_3$ | |

Table 2: Compounds of the general formula (I) according to the invention, where A is A1, $R^6$ is methyl, R is CH(Me)OCO$_2$Me, W is CY and V is hydrogen. Table 2 comprises 451 compounds (2-1 to 2-451) in which X, Y and Z have the meanings as defined in Table 1.

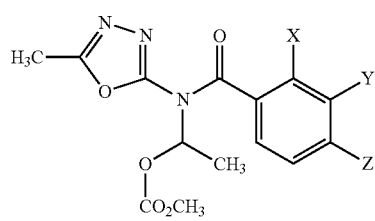

Table 3: Compounds of the general formula (I) according to the invention, where A is A1, $R^6$ is methyl, R is CH(Me)OCO$_2$-c-hexyl, W is CY and V is hydrogen. Table 3 comprises 451 compounds (3-1 to 3-451) in which X, Y and Z have the meanings as defined in Table 1.

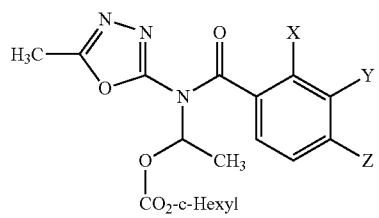

Table 4: Compounds of the general formula (I) according to the invention, where A is A2, $R^6$ is methyl, R is CH(Me)OCO$_2$Et, W is CY and V is hydrogen. Table 4 comprises 451 compounds (4-1 to 4-451) in which X, Y and Z have the meanings as defined in Table 1.

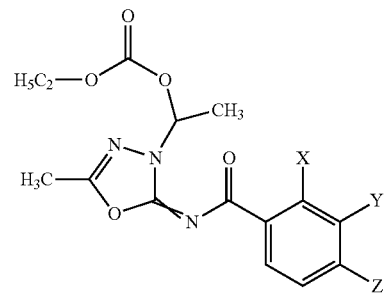

Table 5: Compounds of the general formula (I) according to the invention, where A is A2, $R^6$ is methyl, R is CH(Me)OCO$_2$Me, W is CY and V is hydrogen. Table 5 comprises 451 compounds (5-1 to 5-451) in which X, Y and Z have the meanings as defined in Table 1.

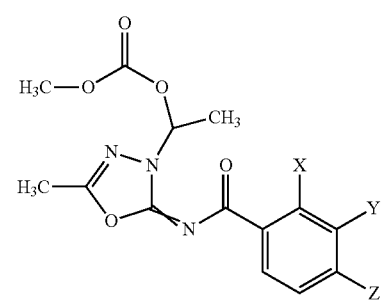

Table 6: Compounds of the general formula (I) according to the invention, where A is A2, $R^6$ is methyl, R is CH(Me)OCO$_2$-c-hexyl, W is CY and V is hydrogen. Table 6 comprises 451 compounds (6-1 to 6-451) in which X, Y have the meanings as Z are defined in Table 1.

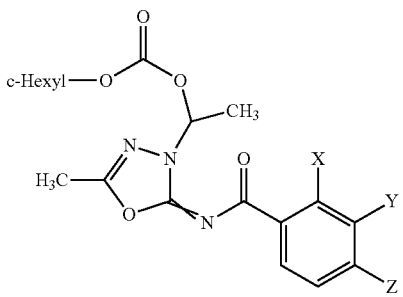

Table 7: Compounds of the general formula (I) according to the invention, where A is A3, R⁶ is methyl, R is CH(Me)OCO₂Et, W is CY and V is hydrogen. Table 7 comprises 451 compounds (7-1 to 7-451) in which X, Y and Z have the meanings as defined in Table 1.

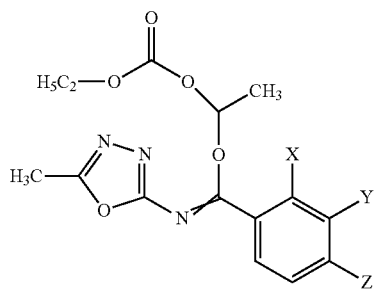

Table 8: Compounds of the general formula (I) according to the invention, where A is A3, R⁶ is methyl, R is CH(Me)OCO₂Me, W is CY and V is hydrogen. Table 8 comprises 451 compounds (8-1 to 8-451) in which X, Y and Z have the meanings as defined in Table 1.

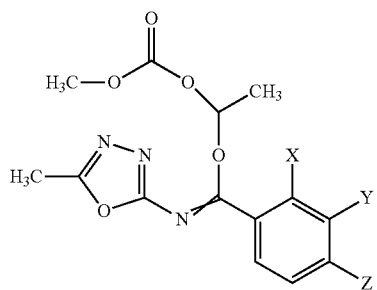

Table 9: Compounds of the general formula (I) according to the invention, where A is A3, R⁶ is methyl, R is CH(Me)OCO₂-c-hexyl, W is CY and V is hydrogen. Table 9 comprises 451 compounds (9-1 to 9-451) in which X, Y and Z have the meanings as defined in Table 1.

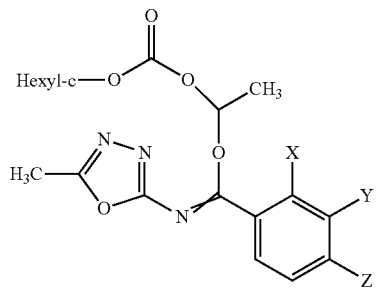

TABLE 10

Compounds of the general formula (I) according to the invention, where A is A1, W is N, R⁶ is methyl and V is hydrogen, and R, X and Z have the definitions specified in Table 10

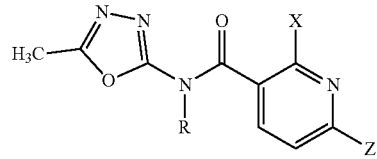

| No. | X | Z | R | Physical data ($^1$H NMR, DMSO-$d_6$, 400 MHz) |
|---|---|---|---|---|
| 10-1 | Cl | CF₃ | CH(Me)OCO₂Et | |
| 10-2 | Cl | CF₃ | CH(Me)OCO₂Me | |
| 10-3 | Cl | CF₃ | CH(Me)OCO₂-c-hexyl | |
| 10-4 | Cl | CF₃ | CH₂OCO₂Et | |
| 10-5 | Cl | CF₃ | CH₂OCO₂Me | |
| 10-6 | Cl | CF₃ | CH₂OCO₂-c-hexyl | |
| 10-7 | Br | CF₃ | CH(Me)OCO₂Et | |
| 10-8 | Br | CF₃ | CH(Me)OCO₂Me | |
| 10-9 | Br | CF₃ | CH(Me)OCO₂-c-hexyl | |
| 10-10 | Br | CF₃ | CH₂OCO₂Et | |
| 10-11 | Br | CF₃ | CH₂OCO₂Me | |
| 10-12 | Br | CF₃ | CH₂OCO₂-c-hexyl | |
| 10-13 | Me | CF₃ | CH(Me)OCO₂Et | |
| 10-14 | Me | CF₃ | CH(Me)OCO₂Me | |
| 10-15 | Me | CF₃ | CH(Me)OCO₂-c-hexyl | |
| 10-16 | Me | CF₃ | CH₂OCO₂Et | |
| 10-17 | Me | CF₃ | CH₂OCO₂Me | |
| 10-18 | Me | CF₃ | CH₂OCO₂-c-hexyl | |
| 10-19 | CH₂OMe | CF₃ | CH(Me)OCO₂Et | |
| 10-20 | CH₂OMe | CF₃ | CH(Me)OCO₂Me | |
| 10-21 | CH₂OMe | CF₃ | CH(Me)OCO₂-c-hexyl | |
| 10-22 | CH₂OMe | CF₃ | CH₂OCO₂Et | |
| 10-23 | CH₂OMe | CF₃ | CH₂OCO₂Me | |
| 10-24 | CH₂OMe | CF₃ | CH₂OCO₂-c-hexyl | |
| 10-25 | CH₂OCH₂CH₂OMe | CF₃ | CH(Me)OCO₂Et | |
| 10-26 | CH₂OCH₂CH₂OMe | CF₃ | CH(Me)OCO₂Me | |
| 10-27 | CH₂OCH₂CH₂OMe | CF₃ | CH(Me)OCO₂-c-hexyl | |
| 10-28 | CH₂OCH₂CH₂OMe | CF₃ | CH₂OCO₂Et | |
| 10-29 | CH₂OCH₂CH₂OMe | CF₃ | CH₂OCO₂Me | |
| 10-30 | CH₂OCH₂CH₂OMe | CF₃ | CH₂OCO₂-c-hexyl | |

Table 11: Compounds of the general formula (I) according to the invention, where A is A2, W is N, R⁶ is methyl and V is hydrogen. Table 11 comprises 30 compounds (11-1 to 11-30) in which R, X and Z have the meanings as defined in Table 10.

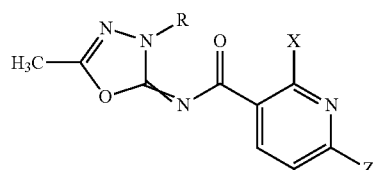

Table 12: Compounds of the general formula (I) according to the invention, where A is A3, W is N, R⁶ is methyl and V is hydrogen. Table 12 comprises 30 compounds (12-1 to 12-30) in which R, X and Z have the meanings as defined in Table 10.

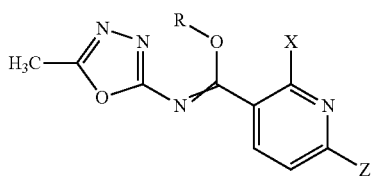

The Abbreviations Used Mean:

| | | | |
|---|---|---|---|
| Et = ethyl | Me = methyl | n-Pr = n-propyl | i-Pr = isopropyl |
| c-Pr = cyclopropyl | Ph = phenyl | Bn = benzyl | Bu = butyl |
| c = cyclo | | | |

B. Formulation Examples a) A dusting product is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
75 parts by weight of a compound of the formula (I),
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate
2 parts by weight of sodium oleoylmethyltaurate,
1 part by weight of polyvinyl alcohol
17 parts by weight of calcium carbonate and
50 parts by weight of water,
then grinding the mixture in a bead mill and atomizing and drying the resulting suspension in a spray tower by means of a one-phase nozzle.

C. Biological Examples

1. Pre-Emergence Herbicidal Action Against Harmful Plants

Seeds of monocotyledonous and dicotyledonous weed plants and crop plants are laid out in wood-fiber pots in sandy loam and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). Here, for example, the compounds Nos. 1-145, 1-385, 3-385, 4-145, 4-385, 6-385, 7-145, 7-385 and 9-385, at an application rate of 320 g/ha, each show an activity of at least 80% against *Stellaria media* and *Veronica persica*.

2. Post-Emergence Herbicidal Action Against Harmful Plants

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). Here, for example, the compounds Nos. 1-145, 1-385, 3-385, 4-145, 4-385, 6-385, 7-145, 7-385 and 9-385, at an application rate of 80 g/ha, each show an activity of at least 80% against *Stellaria media* and *Amaranthus retroflexus*.

3. Comparative Experiment in Pre-Emergence

For comparative purposes, the herbicidal activity of some compounds according to the invention and the most structurally similar compounds known from the prior art were tested.

| Compound | Dosage [g/ha] | Herbicidal activity against ALOMY |
|---|---|---|
| No. 7-385, inventive | 80 | 90% |
| No. 2-360, from WO 2012/126932 | 80 | 70% |
| No. 3-385, inventive | 80 | 100% |
| No. 2-360, from WO 2012/126932 | 80 | 70% |
| No. 9-385, inventive | 80 | 90% |
| No. 2-360, from WO 2012/126932 | 80 | 70% |
| No. 1-145, inventive | 80 | 100% |
| No. D-001, from WO 2013/087577 | 80 | 0% |

The experiments show, by way of example, the superior herbicidal activity of the compounds according to the invention on the harmful plant *Alopecurus myosuroides* (ALOMY).

The invention claimed is:
1. An N-(1,3,4-oxadiazol-2-yl)arylcarboxamide derivative of formula (I)

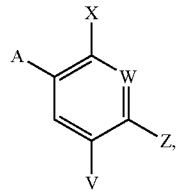

wherein the symbols and indices are each defined as follows:
W is N or CY,
X and Z are each independently hydrogen, nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1R^2$, or $P(O)(OR^5)_2$, or
heteroaryl, heterocyclyl or phenyl, each substituted by s radicals selected from the group consisting of methyl, ethyl, methoxy, nitro, trifluoromethyl and halogen,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $CO_2R^1$, $OCO_2R^1$, $NR^1CO_2R^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$CN$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $CH=NOR^1$, $(C_1-C_6)$-alkyl-$CH=NOR^1$, or $(C_1-C_6)$-alkyl-O—N=$C(R^1)_2$, or
$(C_1-C_6)$-alkylphenyl, $(C_1-C_6)$-alkylheteroaryl, $(C_1-C_6)$-alkylheterocyclyl, phenyl, heteroaryl or heterocyclyl, each substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and wherein heterocyclyl bears n oxo groups,
or
Y and Z together with the two atoms to which they are bonded form a 5-, 6- or 7-membered, unsaturated, partly saturated or saturated ring which, as well as carbon atoms, in each case has s nitrogen atoms, n oxygen atoms, n sulfur atoms and n $S(O)$, $S(O)_2$, C=N—$R^8$, $C(OR^9)_2$, C[—O—$(CH_2)_2$—O—] or C(O) elements as ring members,
wherein the carbon atoms are substituted in each case by s radicals selected from the group consisting of halogen, cyano, $(C_1-C_6)$-alkyl, $(C_2-C_{10})$-alkenyl, $(C_2-C_{10})$-alkynyl, $(C_1-C_6)$-haloalkyl, $(C_1-C_6)$-alkoxy, phenoxy, halo-$(C_1-C_6)$-alkoxy, $(C_3-C_8)$-cycloalkyl, $(C_2-C_8)$-alkoxyalkyl and phenyl,
wherein the nitrogen atoms are substituted in each case by n radicals selected from the group consisting of $(C_1-C_6)$-alkyl and phenyl,
and in which the aforementioned phenyl radicals are substituted in each case by s radicals selected from the group consisting of cyano, nitro, halogen, $(C_1-C_6)$-alkyl, $(C_1-C_6)$-haloalkyl and $(C_1-C_6)$-alkoxy,
V is hydrogen, nitro, halogen, cyano, $(C_1-C_4)$-alkyl, $(C_1-C_4)$-haloalkyl, $OR^1$ or $S(O)_nR^2$,
$R^1$ is hydrogen, or
$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, each substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and wherein heterocyclyl bears n oxo groups,
$R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, each substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and wherein heterocyclyl bears n oxo groups,
$R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl,
$R^4$ is $(C_1-C_6)$-alkyl, $(C_2-C_6)$-alkenyl or $(C_2-C_6)$-alkynyl, $(C_3-C_6)$-cycloalkyl or $(C_3-C_6)$-cycloalkyl-$(C_1-C_6)$-alkyl,
$R^5$ is $(C_1-C_4)$-alkyl,
n is 0, 1 or 2,
s is 0, 1, 2 or 3,
A is an A1, A2, or A3 radical

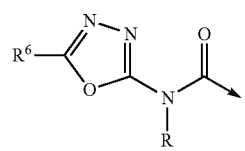

A1

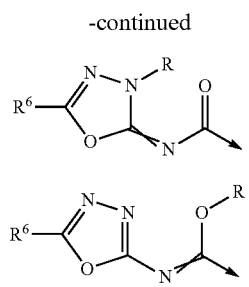

R is (C$_1$-C$_6$)-alkyl-OC(O)N(R$^3$)$_2$ or (C$_1$-C$_6$)-alkyl-OC(O)OR$^{10}$, R$^6$ is hydrogen, or (C$_1$-C$_6$)-alkyl, R$^1$O—(C$_1$-C$_6$)-alkyl, CH$_2$R$^7$, (C$_3$-C$_7$)-cycloalkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, OR$^1$, NHR$^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, or methylsulfonyl, or heteroaryl, heterocyclyl, benzyl or phenyl, each substituted by s radicals selected from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, R$^7$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, (C$_1$-C$_6$)-alkoxy, or (C$_3$-C$_6$)-cycloalkyl, or heteroaryl, heterocyclyl or phenyl, each substituted by s radicals from the group consisting of methyl, ethyl, methoxy, trifluoromethyl and halogen, R$^8$ is (C$_1$-C$_6$)-alkyl, halo-(C$_1$-C$_6$)-alkyl, (C$_1$-C$_6$)-alkoxy or halo-(C$_1$-C$_6$)-alkoxy, R$^9$ is (C$_1$-C$_6$)-alkyl or halo-(C$_1$-C$_6$)-alkyl, and R$^{10}$ is (C$_1$-C$_6$)-alkyl, halo-(C$_1$-C$_6$)-alkyl or (C$_1$-C$_6$)-cycloalkyl.

2. The N-(1,3,4-oxadiazol-2-yl)arylcarboxamide derivative of the formula (I) as claimed in claim 1, wherein R$^6$ is hydrogen, (C$_1$-C$_6$)-alkyl, R$^1$O—(C$_1$-C$_6$)-alkyl, halo-(C$_1$-C$_6$)-alkyl, or (C$_2$-C$_6$)-alkenyl.

3. The N-(1,3,4-oxadiazol-2-yl)arylcarboxamide derivative of the formula (I) as claimed in claim 1, wherein W is CY, X and Z are each independently hydrogen, halogen, (C$_1$-C$_6$)-alkyl, (C$_1$-C$_6$)-haloalkyl, (C$_2$-C$_6$)-alkenyl, (C$_3$-C$_6$)-cycloalkyl, (C$_3$-C$_6$)-halocycloalkyl, OR', S(O)$_n$R$^2$, SO$_2$N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, or heteroaryl, heterocyclyl or phenyl, each substituted by s radicals selected from the group of methyl, ethyl, methoxy, nitro, trifluoromethyl and halogen, Y is hydrogen, (C$_2$-C$_6$)-alkenyl, COR$^1$, CO$_2$R$^1$, OCO$_2$R$^1$, NR$^1$CO$_2$R$^1$, C(O)N(R$^1$)$_2$, NR$^1$C(O)N(R$^1$)$_2$, OC(O)N(R$^1$)$_2$, C(O)N(R$^1$)OR$^1$, NR$^1$SO$_2$R$^2$, NR$^1$COR$^1$, OR$^1$, S(O)$_n$R$^2$, SO$_2$N(R$^1$)$_2$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-CO$_2$R$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, N(R$^1$)$_2$, CH=NOR$^1$, or (C$_1$-C$_6$)-alkyl-CH=NOR$^1$, or (C$_1$-C$_6$)-alkylheteroaryl, (C$_1$-C$_6$)-alkylheterocyclyl, heteroaryl or heterocyclyl, each substituted by s radicals selected from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy, (C$_1$-C$_6$)-alkoxy-(C$_1$-C$_4$)-alkyl and cyanomethyl, and where heterocyclyl bears n oxo groups, V is hydrogen, Cl, OMe, methyl or ethyl, and R$^6$ is methyl, ethyl, methoxymethyl or methoxyethyl.

4. The N-(1,3,4-oxadiazol-2-yl)arylcarboxamide derivative of the formula (I) as claimed in claim 1, wherein X is F, Cl, Br, methyl, ethyl, cyclopropyl, trifluoromethyl, methoxy, methoxymethyl, methoxyethoxymethyl, SMe or SO$_2$Me, Z is hydrogen, F, Cl, Br, I, methyl, ethyl, trifluoromethyl, difluoromethyl, pentafluoroethyl, methylsulfonyl or ethylsulfonyl, Y is hydrogen, SMe, S(O)Me, SO$_2$Me, SEt, S(O)Et, SO$_2$Et, CH$_2$OMe, CH$_2$OEt, CH$_2$OCH$_2$CF$_3$, CH$_2$SMe, CH$_2$S(O)Me, CH$_2$SO$_2$Me, vinyl, C(O)Me, C(O)Et, C(O)cPr, CO$_2$Me, CHN=OMe, 4,5-dihydro-1,2-oxazol-3-yl, 5-methyl-4,5-dihydro-1,2-oxazol-3-yl, 5-methyl-4,5-dihydro-1,2-oxazol-3-yl, 5-cyanomethyl-4,5-dihydro-1,2-oxazol-3-yl, 4,5-dihydro-1,2-oxazol-5-yl, 3-methyl-4,5-dihydro-1,2-oxazol-5-yl, 1H-pyrazol-1-yl, 1H-1,2,3-triazol-1-yl, 2H-1,2,3-triazol-2-yl, 1H-1,2,4-triazol-1-yl, pyrolidin-2-on-1-yl, morpholin-3-on-4-yl, OMe, OEt, OnPr, OCH$_2$cPr, OCH$_2$CH$_2$F; OCH$_2$CH$_2$OMe or OCH$_2$CH$_2$CH$_2$OMe, V is hydrogen, R is CH$_2$OCO$_2$Et, CH(CH$_3$)OCO$_2$Me, CH(CH$_3$)OCO$_2$Et, CH(CH$_3$)OCO$_2$-c-hexyl, CH(CH$_3$)OCO$_2$-i-Pr or CH(CH$_3$)OCO$_2$-t-Bu, and R$^6$ is methyl.

5. A herbicidal composition comprising a herbicidally effective amount of at least one N-(1,3,4-oxadiazol-2-yl)arylcarboxamide derivative of the formula (I) as claimed in claim 1.

6. The herbicidal composition as claimed in claim 5 further comprising one or more formulation auxiliaries.

7. The herbicidal composition as claimed in claim 5, further comprising at least one pesticidally active substance selected from the group consisting of insecticides, acaricides, herbicides, fungicides, safeners, and growth regulators.

8. The herbicidal composition as claimed in claim 7, wherein the at least one pesticidally active substance is a safener.

9. The herbicidal composition as claimed in claim 7, wherein the at least one pesticidally active substance is a herbicide.

10. The herbicidal composition as claimed in claim 5, further comprising cyprosulfamide, cloquintocet-mexyl, mefenpyr-diethyl or isoxadifen-ethyl.

11. A method of controlling unwanted plants, comprising applying an effective amount of at least one compound of the formula (I) as claimed in claim 1 or of a herbicidal composition thereof to the plants or to a site of unwanted vegetation.

12. The method as claimed in claim 11, wherein the unwanted plants are in one or more crops of useful plants.

13. The method as claimed in claim 12, wherein the useful plants are transgenic useful plants.

\* \* \* \* \*